US006863529B2

(12) United States Patent
Strong et al.

(10) Patent No.: US 6,863,529 B2
(45) Date of Patent: Mar. 8, 2005

(54) DENTAL DRILL SYSTEM AND METHOD OF USE

(75) Inventors: J. Todd Strong, Birmingham, AL (US); Carl E. Misch, Detroit, MI (US); George Beck, Pueblo, CO (US)

(73) Assignee: Biohorizons Implant Systems, Inc., Birmingham, AL (US)

( * ) Notice: Subject to any disclaimer, the term of this patent is extended or adjusted under 35 U.S.C. 154(b) by 145 days.

(21) Appl. No.: 10/151,376

(22) Filed: May 20, 2002

(65) Prior Publication Data

US 2002/0172923 A1 Nov. 21, 2002

Related U.S. Application Data

(60) Provisional application No. 60/291,831, filed on May 18, 2001.

(51) Int. Cl.[7] .................................................. A61C 3/02
(52) U.S. Cl. ...................................................... 433/165
(58) Field of Search ................................ 433/102, 165; 606/80

(56) References Cited

U.S. PATENT DOCUMENTS

| 4,325,373 A | 4/1982 | Slivenko et al. | 128/303 R |
|---|---|---|---|
| 4,345,899 A | 8/1982 | Vlock | 433/165 |
| 4,676,750 A | 6/1987 | Mason | 433/101 |
| 4,820,156 A | 4/1989 | Ross | 433/165 |
| 4,897,037 A | 1/1990 | Appleby | 433/166 |
| 5,098,293 A | * 3/1992 | Loof et al. | 433/165 |
| 5,741,267 A | * 4/1998 | Jorneus et al. | 606/102 |
| 5,791,902 A | 8/1998 | Lauks | 433/165 |
| 5,839,897 A | 11/1998 | Bordes | 433/165 |
| 5,890,897 A | * 4/1999 | Kruger et al. | 433/75 |
| 5,941,706 A | 8/1999 | Ura | 433/165 |
| 6,146,138 A | * 11/2000 | Dalmau | 433/141 |
| 6,171,312 B1 | * 1/2001 | Beaty | 606/80 |
| 6,179,616 B1 | 1/2001 | Danger | 433/165 |
| 2002/0094508 A1 | * 7/2002 | Lorenzi | 433/165 |

* cited by examiner

Primary Examiner—Cary E. O'Connor
(74) Attorney, Agent, or Firm—Needle & Rosenberg, PC.

(57) ABSTRACT

A dental drill system for use in preparing an osteotomy of a predetermined depth and diameter sized to receive a dental implant therein is disclosed. The drill system comprises at least one elongate depth drill of a first diameter adapted to drill the osteotomy opening to the predetermined depth, and at least one elongate width increasing drill of a second greater diameter adapted to size the diameter of the osteotomy opening to the predetermined diameter. The invention also teaches a method of using the dental drill system to form the osteotomy opening, the method comprising the steps of using a starter drill to define at least a portion of the osteotomy opening, using at least one elongate depth drill of a first diameter to drill the osteotomy opening to the predetermined depth, and using at least one elongate width increasing drill of a second greater diameter greater than the first diameter to increase the diameter of the osteotomy opening to the predetermined diameter.

36 Claims, 3 Drawing Sheets

DENTAL DRILL SYSTEM AND METHOD OF USE

CROSS-REFERENCE TO RELATED APPLICATIONS

This application claims priority to provisional U.S. Patent Application Ser. No. 60/291,831, filed on May 18, 2001, in the United States Patent and Trademark Office, the provisions of which are incorporated herein fully by this reference.

FIELD OF THE INVENTION

The invention relates in general to drills used in dental surgical procedures. More particularly, the invention relates to improved dental drills, a dental drill system, and a method for using same by a dental surgeon in preparing a properly sized osteotomy within a patient's jaw for the receipt of a dental implant therein.

BACKGROUND OF THE INVENTION

The use of dental implants is well known, and dental implants have proven to be a durable and efficient means of replacing a lost tooth. Typically, when a patient breaks a tooth their options are either to have the tooth pulled or crowned. In order to crown a tooth, the root structure of the tooth must be undamaged and properly seated within the jawbone. Thereafter a permanent crown is fabricated by a dental laboratory for being received on and cemented to a prepared portion of the tooth extending above the gum line. Although the use of crowns is well known and accepted, problems may persist with the health of the underlying tooth structure and thus the durability of both the tooth and the crown.

As an alternative to a crown, for example where the tooth has been pulled or is otherwise absent, a dental implant provides a durable and efficient replacement for the missing tooth. In order to receive a dental implant, the dentist or dental surgeon will first prepare an osteotomy in the patient's jawbone for receiving a base portion of the implant therein. Once implanted, the base portion will in time become permanently affixed to the jaw by allowing the tissues surrounding the base portion to grow into and about the base portion for securing it to the patient's jaw. Thereafter an abutment is passed into the base portion, typically by being threaded into the base portion, and a permanent replacement tooth, somewhat akin to a crown, is prepared and permanently affixed to the abutment.

Some of the known problems that arise with the preparation of the osteotomy are that it is being prepared within the limited confines of a patient's mouth, and as such the dental surgeon is oftentimes required to estimate the depth of the opening being drilled into the patient's jawbone, as well as estimating the size, i.e., the diameter, of the opening being formed so that the opening has the necessary width and/or diameter for receiving and seating the base portion of the dental implant therein. Accordingly, the dental surgeon may have to refer to a shallow or faint depth mark scribed or formed directly on the shaft of the drill used to prepare, or drill, the osteotomy in order to determine the depth thereof.

This is an imprecise method, however, of responding to an exacting requirement for ensuring that the implant is properly seated within the patient's jaw, and for avoiding anatomic landmarks such as the patient's mandibular nerve or sinus cavities. Also, once drilled to the proper depth, the osteotomy oftentimes needs to be further drilled to the proper width/diameter for receiving the implant. It must also be borne in mind that this drilling is being done in the jawbone and tissues of a patient, and thus the need remains to minimize the amount of drilling in the jaw to avoid sensitive anatomical areas therein, as well as for patient comfort, healing, and health while ensuring the implant is properly seated in the jaw.

What is needed, therefore, but unavailable in the art is an improved dental drill system and method that will enable a dental surgeon to quickly, efficiently, and properly define an osteotomy to a desired depth and width while otherwise minimizing the amount of invasive drilling, or overdrilling, in the patient's jawbone, and which will also ensure that the osteotomy is properly sized and shaped to satisfactorily receive the desired dental implant therein.

SUMMARY OF THE INVENTION

The present invention provides a new dental drill system, and a method of use therefor, adapted for the preparation of osteotomys. The inventive dental drill system comprises a series of dental drills that are adapted to quickly and accurately allow a dentist or a doctor to efficiently form an osteotomy of a predetermined depth and diameter within a patient, for example within the patient's 's jawbone for receiving a dental implant of known construction therein.

In a first embodiment, the invention comprises a dental drill system for use in forming an osteotomy opening of a predetermined depth and diameter comprising at least one elongate depth drill of a first diameter adapted to drill the osteotomy opening to the predetermined depth, and at least one elongate width increasing drill of a second greater diameter adapted to increase the diameter of the osteotomy opening to the predetermined diameter.

In a second embodiment, the dental drill system comprises a series of elongate depth drills, each of which is sized and shaped to drill the osteotomy opening to the predetermined depth, and a series of elongate width increasing drills, each of which is sized and shaped to increase the diameter of the osteotomy opening to the predetermined diameter.

The dental drill system thus comprises a series of depth drills and of width increasing drills, respectively, with at least one, or a desired plurality of the respective drills having different drill diameters, and the depth drills having a desired range of drilling depths available. The series of depth drills will preferably be sized to form an osteotomy opening in the range of from about 9.0 millimeters in depth to about 15 millimeters, respectively, and may progressively increase in depth increments less that or equal to 1.0 millimeter, respectively. The diameter of the respective depth drills may begin with a diameter of 2.0 millimeters and extend in range up to about 3.0 millimeters in diameter.

A method of using a dental drill system to form an osteotomy opening of a predetermined depth and diameter is also disclosed, the method comprising using a starter drill to define at least a portion of the osteotomy opening, using at least one elongate depth drill of a first diameter to drill the osteotomy opening to the predetermined depth, and using at least one elongate width increasing drill of a second greater diameter greater than the first diameter to increase the diameter of the osteotomy opening to the predetermined diameter.

The respective depth drills may be provided with an annular ring or stop, a marking or series of markings, or recessed grooves formed as a part of or otherwise defined within the body or shank of the drill and be set at a predetermined distance from the drill tip or leading end thereof, as desired, which permits the dental surgeon to accurately drill an initial osteotomy opening to a predetermined depth within the patient's jawbone. The depth of the stop is set to correspond to the length of the dental implant to be placed within the osteotomy. The cutting geometry of the depth drill(s) may be formed as a spade, a flute, or of any desired and known cutting geometry. Additionally, the drill tip geometry of the depth drill is configured such that the drill has end cutting capabilities extending through any standard and desired cutting geometry, to include by way example and not of limitation, an included drill tip angle of 118 to 120 degrees.

A starter drill, which may comprise a standard dental drill or dental round bur, and which may also comprise a depth drill, and which will have a sharp point adapted to hold the drill in position on an exposed bony surface is used to form an initial opening in the jawbone and tissues of the patient's mouth. Thereafter, at least one appropriately sized depth drill is used to drill to, and establish the desired depth of the osteotomy.

Once the osteotomy opening is drilled to the desired depth, at least one width increasing drill, and possibly a series of width increasing drills, each of progressively greater diameter, is used by the dental surgeon to open or widen the osteotomy to the desired diameter corresponding to the diameter of the dental implant to be placed therein. Each respective width increasing drill is passed into the opening created by the depth drill, and together the width increasing drills are used to progressively and accurately increase the width of the osteotomy so that it closely corresponds to the diameter of the dental or surgical implant being placed therein.

In a preferred embodiment, the diameter of the respective width increasing drills may begin with a diameter of 2.0 millimeters, and extend in increments less than or equal to 0.5 millimeters, up to 5.0 millimeters in diameter, or until the final and desired osteotomy diameter is attained. Using this sequence of drills, therefore, the dental surgeon has much improved control over the angulation of the osteotomy. Additionally, the incremental steps of the width increasing drills used in the drilling sequence described above act to reduce any excess heat that may be generated by the process, and to also help to prevent thermal necrosis of the surrounding tissues.

The cutting geometry of the width increasing drill(s) may be shaped and configured as a spade, a flute, or of any other known and desired drill geometry known to the art, or may be formed as a blunt tip. The drill tip of the respective width increasing drills, however, does not have an end cutting geometry so that the absence of a cutting drill tip acts as an auxiliary stop such that the width increasing drills do not otherwise extend or increase the depth of the osteotomy defined within the patient's jaw.

Among the advantages of the inventive dental drill system, therefore, to include the depth drill and the width increasing drills thereof, when compared to conventional dental drills is that the dental surgeon is now provided with the means to greatly improve their control over the formation of the osteotomy. No longer is there a need for the surgeon to rely on estimated depth markings placed or marked on the drill or drills being used in order to reach the desired osteotomy depth, which markings are generally difficult to see during surgery. Rather the disclosed drill system performs this function and removes the imprecision and guesswork, from the process of forming an osteotomy, and permits much greater control of the process and the finished osteotomy.

DETAILED DESCRIPTION

Figure 1:
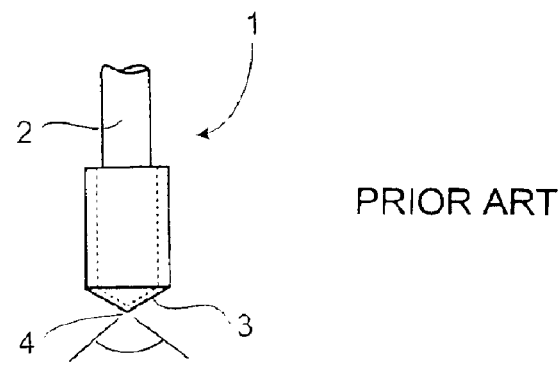
FIG. 1 is a schematic illustration of a conventional dental drill.

Referring now in detail to the drawings, in which like reference numerals indicate like characters throughout the several views, a conventional dental drill 1 is schematically illustrated in FIG. 1. As known, the drill has an elongate body or shank 2 formed about a longitudinal axis, with a cutting geometry 3, also referred to as a cutting region or the cutting flutes, defined on the exterior surface of the drill. The drill ends in a pointed drill tip 4, having an included drill tip angle of any desired and/or standard geometry, which may for example comprise an included angle of approximately 118 degrees. As known, the length of the drill tip is a function of the diameter of the drill bit.

Figures 2, 3:
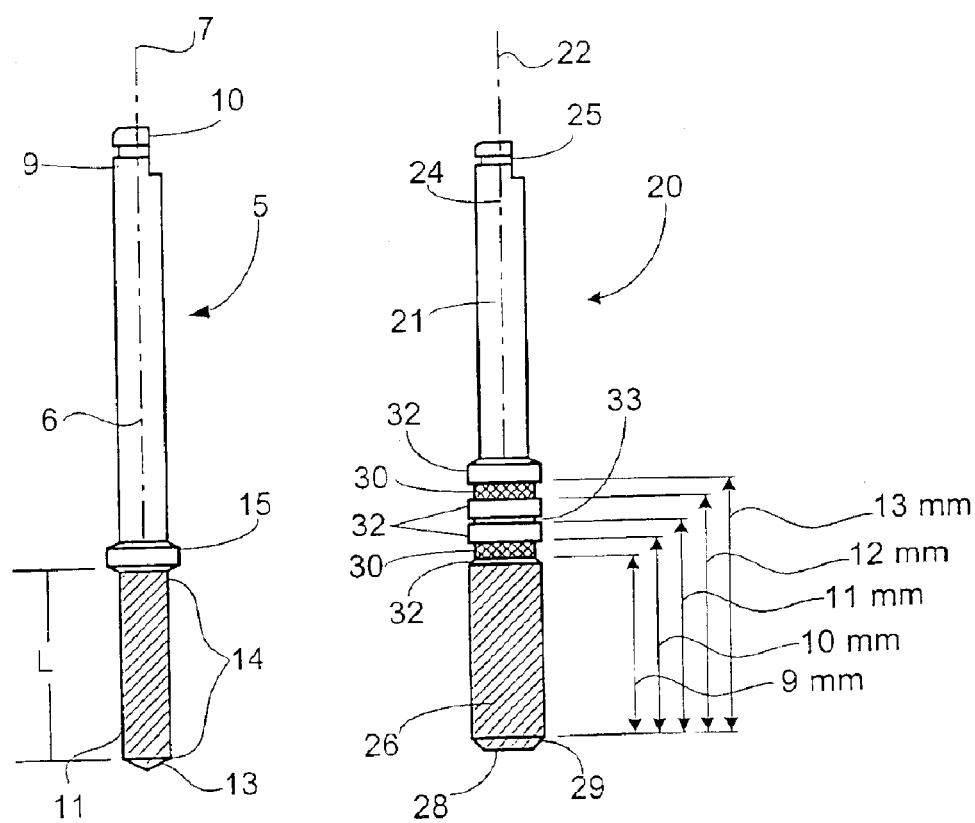
FIG. 2 is an elevational view of a first embodiment of a depth drill adapted for use with the dental drill system of the invention.
FIG. 3 is an elevational view of a first embodiment of a width increasing drill adapted for use with the dental drill system of the invention.

Referring now to FIG. 2, an illustrative depth drill 5 for use with the dental drill system of the invention is illustrated. The depth drill has an elongate body 6 formed about a longitudinal axis 7. The body has a first end 9 at which a conventionally formed right angle latch or drill chuck 10 is provided with any of the known types of dental drill handpieces. It is understood that any conventional drive connection can be formed at the second end of, or on the depth drill, as desired. The body of the depth drill also has a second end 11, at which a drill tip 13 is formed having a cutting geometry 14 extending from the drill tip toward a spaced annular ring or depth stop 15 formed as a part of the drill body.

Preferably, the depth stop or ring 15 is permanently affixed to the drill, i.e., is formed as a part thereof, when the drill is being machined or otherwise formed. The stop is positioned on the body of the drill at a predetermined distance from either of the drill tip, or a transition point defined where the major diameter of the drill body ends and the cutting geometry of the drill bit begins and extends toward the end of the drill tip, as desired. It is also anticipated that the stop ring could be made to be adjustable by being provided with a set screw (not illustrated), for example, and the body of the drill adapted to slidably receive the stop thereover and along its length for being set in the desired depth or stop position, if and as desired. It is further anticipated that the dental drill system may include a series of separate depth drills, each drill being of a differing diameter and depth, respectively, for the purpose of ensuring accurate depth control when the appropriate depth drill is used in forming or otherwise defining an osteotomy within a patient's jawbone and surrounding tissues.

As shown in FIG. 2, the drill tip 13 has an included drill tip angle of approximately 118 degrees, which angle may be increased or decreased, as desired. The depth stop 15 may be machined as a part of the drill itself, i.e. turned when the drill is formed, or affixed to the body of the drill after the cutting geometry has been defined thereon. The cutting geometry 14 extending from the drill tip to the stop can be of any desired shape and form, which may, for example, comprise a helical or a fluted drill, a spade bit, or any other type of drill that is adapted for use in drilling through human tissue and bone.

Although only one illustrative depth drill is shown in FIG. 1, again, it is anticipated that a series of depth drills will be provided of varying depth and diameter corresponding to the length and diameter, respectively, of the dental implant to be placed within the osteotomy being formed. For example, and not by way of limitation, it is anticipated that two depth drills may be provided having a depth of 9 millimeters, represented by the reference character "L" in FIG. 2, extending from the drill tip to the stop, the two respective depth drills having a diameter of 2.0 and 2.5 millimeters, respectively.

Similarly, two additional depth drills may also be provided as a part of the drill system, also having drill diameters of 2.0 and 2.5 millimeters, respectively, but with a depth stop set at a 12 millimeter depth. The diameter of the respective depth drills may therefore begin with a diameter of 2.0 millimeters and extend in range up to about 3.0 millimeters in diameter, as desired. Thus, it can be seen, and it is the intent of this invention, that any number of desired depth drills can be provided, of any desired depth and drill diameter, and each of which will be constructed in the fashion described herein.

Accordingly, the dental drill system comprises at least one or a series of depth drills with at least one, or a desired plurality of the respective drills having different drill diameters, and the depth drills having a desired range of drilling depths available. The series of depth drills will preferably be sized to form an osteotomy opening in the range of from about 9.0 millimeters in depth to about 15 millimeters, respectively, and may progressively increase in depth increments less that or equal to 1.0 millimeter, respectively.

Figure 8:
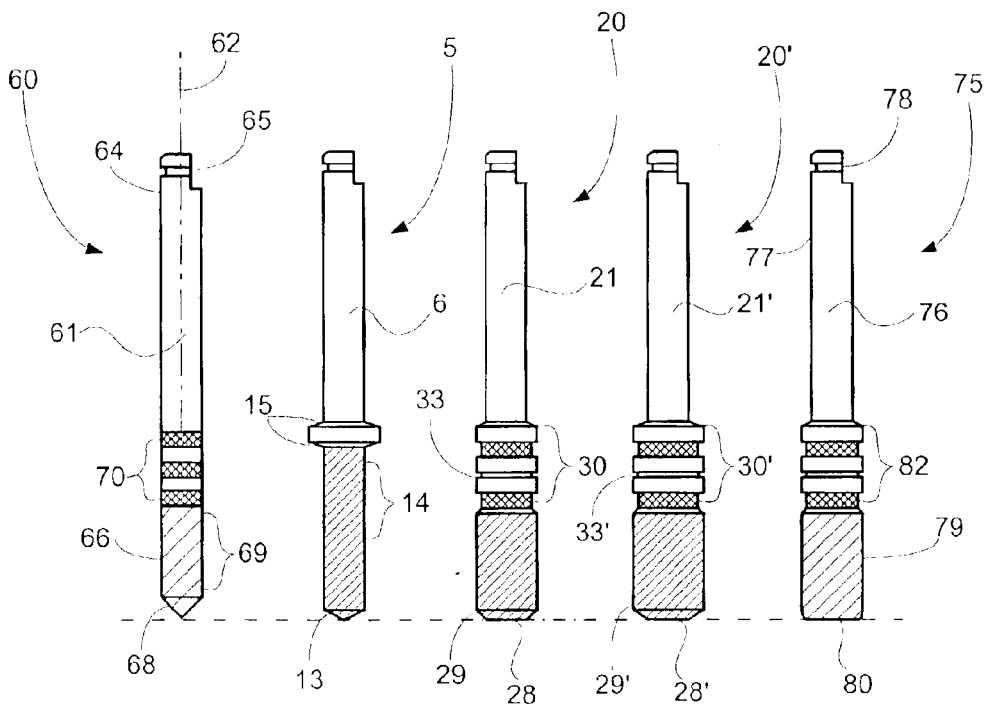
FIG. 8 is a schematic illustration of the several dental drills that comprise a preferred embodiment of the dental drill system of the invention.

Referring now to FIGS. 3 and 8, a first embodiment of a width increasing drill 20 of the dental drill system is illustrated. The width increasing drill has an elongate body 21 formed about a longitudinal axis 22, with a first end 24 at which a conventional right angle latch or chuck 25 is formed. Although a right angle latch is illustrated, as known to those of skill in the art, any known type of latch, chuck, or drive connection may be used in place of the right angle latch or chuck, as desired, for any of the several embodiments of the depth and width increasing drills of the invention. So constructed, the right angle latch, or other drive connection, for both of the depth and the width increasing drills can be readily affixed to any of the known types of dental drill handpieces currently in use, and as may be developed in the future.

Figures 4, 5A, 5B:
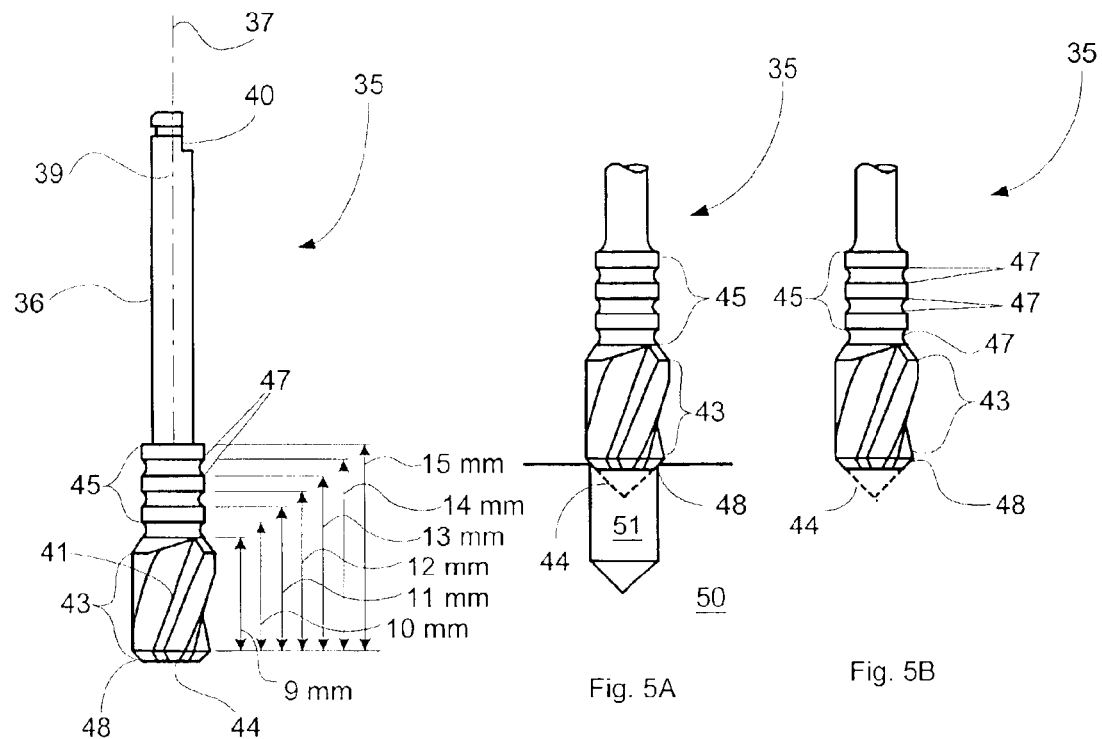
FIG. 4 is an elevational view of a second embodiment of a width increasing drill adapted for use with the dental drill system of the invention.
FIG. 5A is a partial elevational view of the width increasing drill of FIG. 4 positioned with respect to an initial osteotomy opening defined by a depth drill.
FIG. 5B is a partial elevational view of the width increasing drill of FIG. 4 illustrating the differences between a standard dental drill or a depth drill used to form an osteotomy.

The width increasing drill 20 has a second end 26, at which a flat, a straight, or a "blunt" drill tip 28 is defined. The cutting geometry 29 of the drill tip is defined at and about a limited portion of the exterior periphery of the second end, only, of the width increasing drill and extends in the lengthwise direction of the drill a predetermined distance from the drill tip. The remainder of the shank or body of the width increasing drill, as illustrated, extends in the lengthwise direction of the drill and is not adapted to further cut or drill the osteotomy within the patient. Accordingly, and as illustrated in FIG. 5A, and schematically in FIGS. 10B and C, the width increasing drill is used only to increase the diameter of the osteotomy 51 (FIG. 7), and not to increase the depth thereof. The depth of the osteotomy is controlled solely by the starter drill, if one is used, and the depth drill. Additionally, aside from the cutting geometry of the width increasing drill, the remainder of the width increasing drill body may be smooth-surfaced if so desired.

Accordingly, the cutting geometry of the width increasing drill is constructed, as described below, such that the width increasing drill acts to remove material only from the sides of the osteotomy, but does not otherwise increase the depth of the osteotomy. By removing the pointed drill bit or section of the second end of the drill (FIGS. 5A and 5B), a dental surgeon can now use the novel width increasing drill(s) of this system to increase the diameter of an osteotomy without otherwise drilling more deeply into any sensitive anatomical areas about the osteotomy opening, for example adjacent teeth, root structures, and or nerves. The cutting geometry 29 can again be of any desired conventional cutting geometry, for example the cutting geometry may comprised a spiral, a helical, as well as a spade bit, or any other known type of cutting geometry that can be adapted for use in penetrating human bone and tissue.

The width increasing drill 20 also includes a series of spaced and recessed annular depth grooves 30 extending in the lengthwise direction of the drill body, each depth groove being formed in and about the drill body at a respective and predetermined distance measured from the drill tip. The depth grooves are defined within the body of the width increasing drill at a predetermined distance from either of the drill tip, or a transition point defined where the major diameter of the drill body ends and the cutting geometry of the drill bit begins and extends toward the end of the drill tip, as desired.

Each one of the depth grooves is defined by a pair of opposed shoulders 32 within the body of the drill. By way of example and not of limitation, the illustrated shoulders 32 may be defined at lengths of 9, 10, 11, 12, 13, 14 and 15 millimeters, respectively, from the flat end of the drill tip 28, as illustrated in FIGS. 3 and 4, in which two embodiments of the width increasing drill are illustrated. Still referring to FIG. 3, the shoulders 32 also define a center-most depth groove 30. The center-most depth groove 33 is preferably set at a distance or depth of 11 millimeters from the drill tip, and acts as a centering guide or marker such that the dental surgeon knows that they are at the center of the 10 and 12 mm depth marks, respectively. Accordingly, the surgeon can quickly gauge the level to which the width increasing drill has been inserted into the osteotomy in expedient fashion, especially during dental surgery.

Incorporating the depth grooves in the shaft of the width increasing drill bit, spaced above the cutting flutes thereof, improves the visualization of the depth markings. The grooves may be conventionally marked, i.e. they may be painted, laser marked, and/or electro-chemically etched on the drill body as desired. Also, and if desired, the grooves may be marked in differing colors corresponding to the respective depths in order to enhance the visibility thereof. Depth grooves such as these are thus likely to be seen more easily during surgery when blood and body tissues are present. Moreover, the glare of the light used during surgery does not affect the visualization of the grooves, as commonly occurs with the known types of surface markings.

A second embodiment of a width increasing drill 35 of the dental drill system is illustrated in FIGS. 4 through 7. The width increasing drill 35 has an elongate body 36 formed about a longitudinal axis 37, with a first end 39 at which a conventional right angle latch or chuck 40, or other desired drive connection/construction, is formed. The width increasing drill 35 has a second end 41, at which a flat drill tip 44 is defined.

A cutting geometry 43 is defined about the exterior periphery, and at the second end of the drill, i.e., the drill tip, extending in the lengthwise direction thereof, and is constructed as described herein such that the width increasing drill acts to remove material only from the sides of the osteotomy opening, and not to otherwise increase the depth of the osteotomy, as discussed above. The cutting geometry 43 can again be of any desired and/or conventional cutting geometry, for example it may comprise a spiral, a helical, or a spade bit, or any other known type of cutting geometry that can be adapted for use in penetrating human bone and tissue.

As with the depth measuring drills, the width increasing drill 35 also includes a series of spaced and recessed annular depth grooves 45, each of which is formed at a respective and predetermined distance measured from the drill tip, and are spaced from one another in series in the lengthwise direction of the drill body. The depth grooves are defined within the body of the width increasing drill at a predetermined distance from either of the drill tip, or a transition point defined where the major diameter of the drill body ends and the cutting geometry of the drill bit begins and extends toward the end of the drill tip, as desired. Each one of the depth grooves is defined by a pair of opposed shoulders 47 separately defined within the body of the drill. As illustrated, and by way of example and not of limitation, the shoulders 47 are formed at a length of 9, 10, 11, 12, 13, 14 and 15 millimeters, respectively, from the flat end of the drill tip 44.

Although a single width increasing drill 20, 35 is illustrated in FIGS. 3 and 4, respectively, it is anticipated that a series of width increasing drills will be provided as a part of the dental drill system hereof, starting, for example, with a width increasing drill diameter of 2.0 millimeters and extending up to and through a range of diameters of less than or equal to 0.5 mm increments, respectively, ending with a drill diameter of 5.0 millimeters, or of any other desired diameter corresponding to the diameter of the dental implant to be placed within the osteotomy. As known, the "corresponding" diameter of the dental implant will not necessarily be the same diameter formed by the respective width increasing drill(s), as for example the diameter of the dental implant may be 4.0 mm, but the final drilled diameter may be 3.5 mm, depending on the quality, i.e. the hardness, of the patient's bone, the implant design, and to what extent an interference fit of the implant within the osteotomy is desired.

The respective width increasing drills of this series of drills will thus preferably increase in increments less than or equal to 0.5 millimeters, such that a series of 2.0, 2.5, 3.0, 3.5, 4.0, 4.5, and 5.0 millimeter diameter width increasing drills will be provided, each of which may be similarly constructed, or may be constructed differently, i.e., having a different cutting geometry, as desired or as necessary.

Figures 6A, 6B, 7:
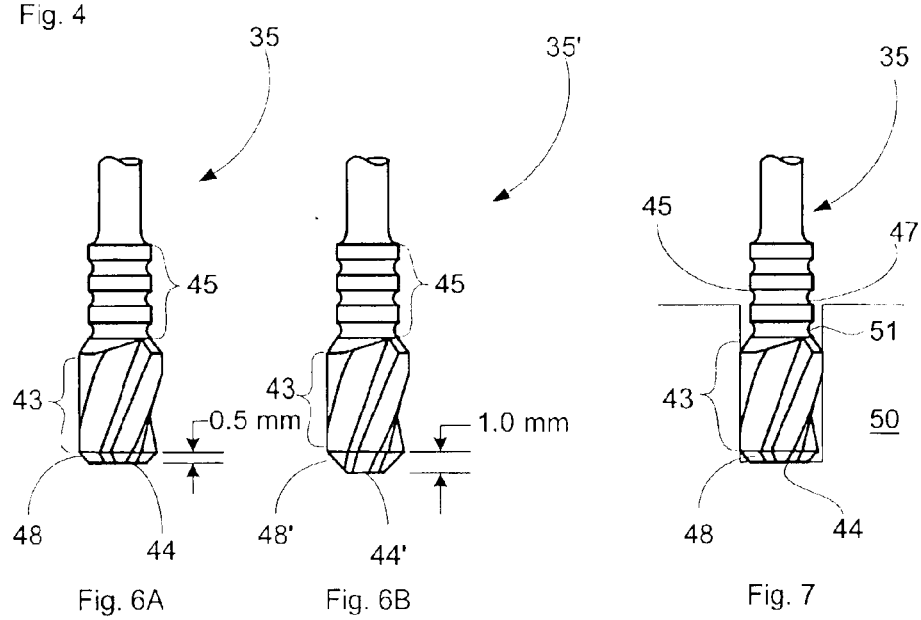
FIG. 6A is a partial elevational view of the width increasing drill of FIG. 4 illustrating a first end cutting region.
FIG. 6B is a partial elevational view of an alternate embodiment of the width increasing drill of FIG. 4 having a second end cutting region.
FIG. 7 is a partial elevational view of the drill tip of the width increasing drill of FIG. 4 received within a schematically illustrated osteotomy opening.

Each of the respective flat-tip width increasing drills of FIGS. 3–7 has the pointed section of the drill tip removed leaving a 0.5 millimeter to a 1.0 millimeter cutting edge or region 48, 48' available, as illustrated in FIGS. 6A and 6B, respectively. If desired, however, the cutting region may be of any desired length, for example and not by way of limitation, a length in the range of from 0.5 to 1.0 millimeters. This design enhancement works because the width increasing drills are used as a part of a series of drills within a surgical procedure, as described hereinabove.

The first drill, i.e., the "starter drill," used to begin the formation of the osteotomy must have a pointed end or a rounded bur in order to start the hole and to increase the depth thereof to a desired initial depth in the jawbone and surrounding tissues of the patient. Preferably, the starter drill will have a sharp point at its end which is adapted to hold the drill in position on a bony surface, for example the exposed surface of a jawbone, so the drill is properly positioned and held in position thereon as the drilling of the osteotomy is started. By way of example, and not of limitation, the starter drill may comprise a standard #6 round dental bur, or other drill, as desired, and preferably having a sharp point. It is also anticipated that the smaller diameter depth drill, the 2.0 millimeter diameter depth drill, may be used as the starter drill rather than a standard dental drill.

A third embodiment of the width increasing drill 20' is illustrated in FIG. 8. The width increasing drill 20' is formed identically to the width increasing drill 20 described above, with the exception that the diameter of the width increasing drill 20' is progressively greater than that of the drill 20. A third embodiment of a width increasing drill 75 is also illustrated in FIG. 8. Referring now to FIG. 8, the width increasing drill 75 has an elongate body 76 formed about a longitudinal axis, with a first end 77 at which a conventional right angle latch, or chuck, or a suitable or drive connection 78 is formed. The width increasing drill 75 also has a second end 79 at which a flat blunted drill tip 80 is defined.

As for the other embodiments of the width increasing drill 20, 35, respectively, the width increasing drill 75 also has a series of spaced and recessed annular depth grooves 82 extending in the lengthwise direction of the drill body, each depth groove being formed in and about the drill body at a respective and predetermined distance measured from the drill tip. The depth grooves once again are defined within the body of the width increasing drill at a predetermined distance from either of the drill tip, or a transition point defined where the major diameter of the drill body ends and the cutting geometry of the drill bit begins and extends toward the end of the drill tip, as desired.

The width increasing drill 75 differs from the width increasing drills 20, 35 in that here its drill tip 80 is entirely flat or blunted to ensure that the depth of the osteotomy is not increased, and which can be also used to trim the generally cylindrical sidewall of the osteotomy. Again, as for the width increasing drills 20, 20', or 75 may have a smooth-surfaced side wall extending in the lengthwise direction of the drill toward the cutting geometry thereof, if so desired.

A first embodiment of a starter drill 60 is also shown in FIG. 8 as a part of the dental drill system of this invention. The starter drill 60 has an elongate body 61 formed about a longitudinal axis 62, with a first end 64 at which a conventionally formed right angle latch 65, or other drive connection, is formed, and a spaced second end 66 at which a drill tip 68 is formed. The drill tip is of a known type of cutting geometry 69 defined thereon and has a sharp point or leading end, and extends in the lengthwise direction of at least the second end of the drill body. The starter drill may have the same cutting geometry, therefore, as described for the depth drill 5.

As shown in FIG. 8, the starter drill may also be provided with a spaced series of depth markings 70 formed on and extending about the drill body, and spaced in the lengthwise direction thereof. The markings 70 may be marked thereon as described above, or may instead comprise a series of spaced and recessed grooves defined within the drill body or shank in the same fashion as are the grooves 30 for the respective width increasing drills, and are for use by the dental surgeon in drilling the osteotomy to the desired initial depth.

Figure 9:
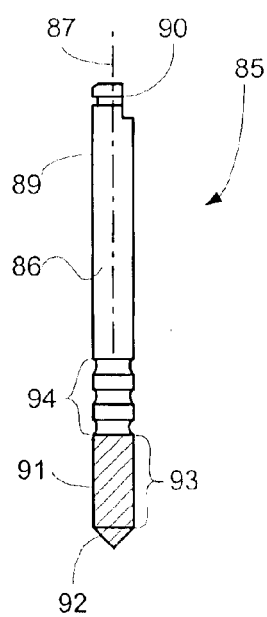
FIG. 9 is an elevational view of a second embodiment of a depth drill adapted for use with the dental drill system of the invention.

A second embodiment of a depth drill 85 of the system is illustrated in FIG. 9. This depth drill 85 may also comprise, or take the place of, the starter drill 60 of FIG. 8. Accordingly, the depth drill 85 has an elongate body 86 formed about a longitudinal axis 87, with a first end 89 at which a conventionally formed right angle latch, or other suitable drive connection, 90 is formed, and a second end 91 at which a drill tip 92 is formed. The drill tip/second end of the depth drill 85 has the cutting geometry 93 as described for depth drill 5, above. Here however, the depth drill does not have a spaced annular ring or depth stop formed as a part of the drill body, rather the drill is provided with a spaced series of recessed annular depth grooves 94 formed about the drill body and spaced in the lengthwise direction thereof as for the width increasing drill(s), discussed above.

The grooves 94 will be formed and/or marked thereon in the same fashion as are the grooves 30 for the respective width increasing drills, discussed above. By forming the depth drill without a fixed stop thereon, the dental surgeon may thus "over prepare" the osteotomy opening beyond the "set" depth, if desired, by drilling beyond the depth of a depth stop in order to countersink the base portion (not illustrated) of the dental implant, for example, within the osteotomy opening.

After the desired depth drill has been used to establish the initial diameter and depth of the osteotomy, the subsequent width increasing drills need only have enough of an end cutting geometry that allows the drills to incrementally increase the osteotomy diameter. This incremental technique of increasing the osteotomy diameter does not utilize the pointed region of the drill, and accordingly it is not needed, as illustrated in FIGS. 5A and B. By eliminating the pointed drill section, i.e., the drill tip, a surgeon can drill deeper without intruding into a sensitive anatomical area and the drill will automatically stop without drilling deeper, and the drill system therefore lessens any "guesswork" in establishing the osteotomy depth and diameter. This may be further enhance by providing the width increasing drills with smooth sides (not illustrated) or the blunt tip of the width increasing drill 75 of FIG. 8, such that only a very limited portion of the width increasing drill is used to cut any bone or tissues within the osteotomy, and the several embodiments of the width increasing drills described herein thus may also be though of as finishing drills.

The manner in which the width increasing drill 35, for example, is received and used within an osteotomy opening 51 defined within a patient's jawbone and surrounding tissues 50 is illustrated in FIG. 7. As shown, the dental surgeon can sight along a selected one of the shoulders 47 of a selected one of the depth grooves 45 to pass the width increasing drill into the osteotomy to the desired depth, here a depth of 11.0 millimeters. Moreover, the depth marks or grooves serve only as a reference, and are not otherwise needed because the drill will "stop" extending into the osteotomy once the flattened or blunted drill tip engages the bottom of the osteotomy defined by the starter or depth drill used.

Figures 10A, 10B, 10C:
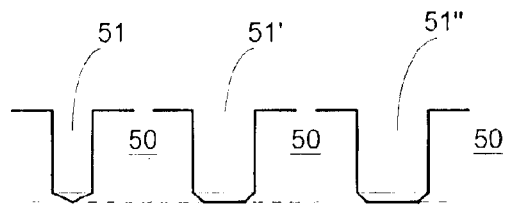
FIGS. 10A–C are schematic illustrations of the manner in which an osteotomy opening, or openings, may be defined using the dental drill system of the present invention.

FIGS. 10A–C schematically illustrate the one, or a pair of separate, osteotomy openings 51, 51' of differing diameters defined within a patient, and illustrates how with the drills provided as a part of the dental drill system of this invention permit a uniform osteotomy depth to be defined within a patient, regardless of the diameter of the osteotomy opening. FIG. 10A illustrates the osteotomy 51 as first formed by the depth drill. The osteotomy is relatively narrow in diameter when compared to the completed osteotomy of FIG. 10C, or to the two osteotomys of FIGS. 10B and C, respectively. FIG. 10B represent either a completed, i.e., sufficiently widened osteotomy 51', or represents a step toward the completion of the second osteotomy 51" of greater diameter illustrated in FIG. 10C. As discussed above, the completed osteotomy(s) will correspond to the diameter of the dental implant to be placed therein.

It is anticipated that each of the respective starter drills, depth drills, and width increasing drills of the drill system disclosed hereinabove will be formed of a surgical grade stainless steel approved for use in dental and surgical procedures, and which is durable and can be easily sterilized for repeated use, and may also therefore be comprised of any suitable material approved for use in surgical procedures and adapted of cutting or drilling bone and tissue.

The process with which the novel drill system of this invention is used is now described. After the patient has been suitably prepared and anesthetized, a starter drill, for example the drill 60 of FIG. 8, or the drill 85 of FIG. 9, or an otherwise standard or conventional dental drill, for example a no. 6 dental round bur, is used by the surgeon to form a small opening within the patient's jawbone and surrounding tissues. Thereafter, the desired depth drill, i.e. a drill having the desired diameter and depth, is used for opening the osteotomy and extending it to the desired depth within the patient's jaw. As described above, this can be readily accomplished by the dental surgeon observing the annular stop or grooves formed on the exterior of the depth drill, and stopping at the appropriate point, on the depth drills as measured by the annular stop (FIG. 2) thereon, or the recessed depth grooves defined therein (FIG. 9).

The dental surgeon will then select the appropriate width increasing drill, or in the alternative a second and wider diameter depth drill, to include the depth drill 85, if desired, or as needed. For example if a 2 millimeter diameter depth drill was used, beginning next with a 2.5 millimeter diameter depth or width increasing drill, and will pass the second drill into the osteotomy opening and to the desired depth by observing the penetration of the drill into the jawbone and tissues of the patient until the desired depth groove 30, 45 and shoulder 32, 47 is reached, or by using a drill with a stop formed thereon or affixed thereto. Thereafter, the drill will be withdrawn, and subsequent width increasing drills of increasing diameter will be used until the desired diameter or width of the osteotomy is attained, all of which will be dependent upon the diameter of the base portion of the dental implant to be positioned within the patient's jaw.

Thus, in fashion heretofore unknown in the art, a dental surgeon is now permitted to quickly and efficiently define an osteotomy within a patient's jawbone with greater accuracy, and which also minimizes the necessity for the physician to estimate how much, and to what depth or diameter, drilling needs to be done within the jawbone for minimizing patient discomfort. Thereafter, and in known fashion, the base portion of the dental implant is passed into the osteotomy and the surrounding bone and tissues are allowed to grow into the base portion for permanently affixing same to the patient's jaw. In a subsequent visit, or visits, to the dentist, an abutment will be threadably passed into the base portion, a replacement tooth will be molded and formed, and the replacement tooth is affixed to the abutment.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the invention. Moreover, although specific terms are employed herein, they are used only in a generic and descriptive sense, and not for the purposes of limiting the described invention.

We claim:

1. A dental drill system for use in forming an osteotomy opening of a predetermined depth and diameter, and which is sized to receive a dental implant therein, said drill system comprising:

at least one elongate depth drill of a first diameter adapted to drill the osteotomy opening to the predetermined depth, the at least one depth drill having a drill tip and a depth stop disposed thereon, said depth stop being spaced from the drill tip a predetermined distance that is substantially equal to the predetermined depth; and at least one elongate width increasing drill of a second greater diameter adapted to increase the diameter of the osteotomy opening to the predetermined diameter, the at least one elongate width increasing drill having a second end and an elongate body, the second end forming a substantially planar surface, a limited portion of the elongate body proximate the second end defining a tapered cutting geometry that extends in the lengthwise direction of the elongate body a predetermined distance ranging from about 0.5 mm to 1.0 mm measured from the second end, wherein the portion of the elongate body extending in the lengthwise direction from the tapered cutting geometry is adapted to for non-operative engagement with the formed surface of the osteotomy within the patient, and wherein, in use, the depth of the osteotomy is controlled by the at least one elongate depth drill of a first diameter and the substantially planar surface of the second end of the at least one elongate width increasing drill is adapted to non-abradingly seat within the formed osteotomy at the predetermined depth.

2. The drill system of claim 1, further comprising at least a second depth drill, wherein the at least one depth drill is sized and shaped to drill the osteotomy opening to a first depth, and the at least one second depth drill is sized and shaped to drill the osteotomy opening to a second depth greater than or equal to the first depth.

3. The drill system of claim 1, the at least one depth drill being sized and shaped to drill the osteotomy opening to a depth in the range of from about 9.0 millimeters to about 15 millimeters.

4. The drill system of claim 1, the at least one depth drill having a drill diameter in the range of from about 2.0 millimeters to about 3.0 millimeters.

5. The drill system of claim 1, the at least one depth drill comprising a series of depth drills constructed and arranged to drill the osteotomy opening depth to a depth ranging from about 9.0 millimeters to about 15 millimeters in increments less than or equal to 1.0 millimeters, respectively.

6. The drill system of claim 1, the at least one depth drill comprising a series of depth drills sized and shaped to drill the osteotomy opening to a depth in the range of from about 9.0 millimeters to about 15 millimeters.

7. The drill system of claim 6, the series of depth drills comprising a plurality of depth drills with diameters ranging from about 2.0 millimeters to about 3.0 millimeters, respectively.

8. The drill system of claim 6, the at least one width increasing drill comprising a series of width increasing drills having a diameter in the range of from about 2.0 millimeters to about 5.0 millimeters, respectively.

9. The drill system of claim 8, the series of width increasing drills increasing in diameter ranging from about 2.0 millimeters to about 5.0 millimeters in increments less than or equal to 0.5 millimeters, respectively.

10. The drill system of claim 1, the at least one depth drill having a drill tip and a series of depth markings disposed thereon and spaced from one another in the lengthwise direction of the at least one depth drill measured approximate the drill tip.

11. The drill system of claim 10, said series of depth markings being constructed and arranged to mark a range of predetermined osteotomy opening depths on the at least one depth drill.

12. The drill system of claim 1, the at least one depth drill having a drill tip, and a series of recessed annular depth grooves defined thereon and being spaced from one another in the lengthwise direction of the at least one depth drill measured approximate the drill tip.

13. The drill system of claim 1, further comprising at least a second width increasing drill, wherein the at least one width increasing drill is constructed and arranged to size the diameter of the osteotomy opening to a first diameter, and the at least one second width increasing drill is constructed and arranged to size the diameter of the osteotomy opening to a second diameter different than the first diameter.

14. The drill system of claim 1, the at least one width increasing drill comprising a series of width increasing drills constructed and arranged to size the diameter of the osteotomy opening to a diameter in the range of from about 2.0 millimeters to about 5.0 millimeters.

15. The drill system of claim 14, the series of width increasing drills increasing in diameter ranging from about 2.0 millimeters to about 5.0 millimeters in increments less than or equal to 0.5 millimeters, respectively.

16. The drill system of claim 1 the at least one width increasing drill having a smooth-surfaced side wall extending toward said cutting geometry.

17. The drill system of claim 1, the at least one width increasing drill having a drill tip, and a series of depth markings disposed thereon and spaced from one another in the lengthwise direction of the at least one width increasing drill spaced from the drill tip.

18. The drill system of claim 1, the at least one width increasing drill having a drill tip, and a series of spaced recessed annular depth grooves defined therein and extending in the lengthwise direction of the at least one width increasing drill spaced from the drill tip.

19. The drill system of claim 1, further comprising at least one starter drill.

20. The drill system of claim 19, the at least one starter drill having a first end with a sharp point defined thereat.

21. The drill system of claim 19, the at least one starter drill being selected from one of the dental drills in the group of drills comprising a conventional dental drill, a dental round bur, and the at least one depth drill.

22. A dental drill system for use in forming an osteotomy opening of a predetermined depth and diameter, and which is sized to receive a dental implant therein, said drill system comprising:
  a series of elongate depth drills, each of which is sized and shaped to drill the osteotomy opening to the predetermined depth, each elongate depth drill having a drill tip and a depth stop disposed thereon, said depth stop being spaced from the drill tip a predetermined distance that is substantially equal to the predetermined depth; and
  a series of elongate width increasing drills, each of which is sized and shaped to increase the diameter of the osteotomy opening to the predetermined diameter, each elongate width increasing drill having a second end and an elongate body, the second end forming a substantially planar surface, a limited portion of the elongate body proximate the second end defining a tapered cutting geometry that extends in the lengthwise direction of the elongate body a predetermined distance ranging from about 0.5 mm to 1.0 mm measured from the second end, wherein the portion of the elongate body extending in the lengthwise direction from the tapered cutting geometry is adapted for non-operative engagement with the formed surface of the osteotomy within the patient, and wherein, in use, the depth of the osteotomy is controlled by the at least one elongate depth drill of a first diameter and the substantially planar surface of the second end of the at least one elongate width increasing drill is adapted to non-abradingly seat within the formed osteotomy at the predetermined depth.

23. The drill system of claim 22, the series of depth drills being constructed and arranged to drill the osteotomy opening depth to a depth ranging from about 9.0 millimeters to about 15 millimeters.

24. The drill system of claim 23, the depth drills increasing in depth from 9.0 millimeters to 15 millimeters in increments less than or equal to 1.0 millimeter, respectively.

25. The drill system of claim 22, the series of depth drills comprising a plurality of depth drills with diameters ranging from about 2.0 millimeters to about 3.0 millimeters, respectively.

26. The drill system of claim 25, the series of depth drills increasing in diameter from 2.0 millimeters to 5.0 millimeters in increments less than or equal to 0.5 millimeters, respectively.

27. The drill system of claim 22, the series of width increasing drills having a diameter in the range of from about 2.0 millimeters to about 5.0 millimeters, respectively.

28. The drill system of claim 27, the series of width increasing drills increasing in diameter from about 2.0 millimeters to about 5.0 millimeters in increments less than or equal to 0.5 millimeters, respectively.

29. The drill system of claim 22, wherein each respective drill of the series of depth drills and the series of width increasing drills, respectively, has a first end with a drill tip defined thereat and a series of depth markings disposed thereon and spaced from one another in the lengthwise direction of each respective drill measured from the first end thereof.

30. The drill system of claim 29, wherein each respective series of depth markings comprises a series of spaced and recessed annular depth grooves extending in the lengthwise direction of the respective drills.

31. A method of using a dental drill system to form an osteotomy opening of a predetermined depth and diameter, said method comprising:
  using a starter drill to define at least a portion of the osteotomy opening;
  providing at least one elongate depth drill having a first diameter, a drill tip and a depth stop disposed thereon, said depth stop being spaced from the drill tip a predetermined distance that is substantially equal to the predetermined depth;
  using the at least one elongate depth drill of the first diameter to drill the osteotomy opening until the depth stop is brought into contact with the tissue of the patient such that the osteotomy opening is drilled to the predetermined depth;
  providing at least one elongate width increasing drill having a second diameter greater than the first diameter, a second end and an elongate body, the second end forming a substantially planar surface, a limited portion of the elongate body proximate the second end defining a tapered cutting geometry that extends in the lengthwise direction of the elongate body a predetermined distance ranging from about 0.5 mm to 1.0 mm measured from the second end, wherein the portion of the elongate body extending in the lengthwise direction from the tapered cutting geometry is adapted to non-operatively engage the formed surface of the osteotomy within the patient;
  using the at least one elongate width increasing drill of the second greater diameter to increase the diameter of the osteotomy opening to the predetermined diameter; and
  inserting the at least one elongate width increasing drill until the substantially planar surface of the second end of the at least one width increasing drill is non-abradingly seated within the formed osteotomy at the predetermined depth.

32. The method of claim 31, the step of using the at least one elongate depth drill further comprising using at least a second depth drill of a third diameter greater than the first diameter and less than the second diameter to drill the osteotomy opening.

33. The method of claim 31, the step of using the at least one elongate width increasing drill further comprising using at least a second width increasing drill of a fourth diameter greater than the second diameter to size the diameter of the osteotomy opening.

34. The method of claim 31, the step of using the starter drill further comprising using the at least one depth drill to define at least a portion of the osteotomy opening.

35. The method of claim 31, the step of using the at least one elongate depth drill further comprising passing the at least one elongate depth drill into the osteotomy opening a distance in the range of from 9.0 millimeters to 15.0 millimeters.

36. The method of claim 31, the step of using the at least one elongate width increasing drill further comprising passing the at least one elongate width increasing drill into the osteotomy opening to size the diameter of the osteotomy opening in the range of from about 2.0 millimeters to about 5.0 millimeters.

* * * * *